United States Patent
Kasprzykowski et al.

(10) Patent No.: US 10,655,464 B2
(45) Date of Patent: May 19, 2020

(54) DEVICE COMPRISING MULTIPLE DETECTORS FOR DETECTING A FLOW OF GAS EXTRACTED FROM A DRILLING FLUID

(71) Applicant: Geoservices Equipements, Roissy en France (FR)

(72) Inventors: Pawel Kasprzykowski, Roissy-en-France (FR); Martin Delacoux Des Roseaux, Roissy-en-France (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 120 days.

(21) Appl. No.: 15/841,713

(22) Filed: Dec. 14, 2017

(65) Prior Publication Data

US 2018/0171786 A1 Jun. 21, 2018

(30) Foreign Application Priority Data

Dec. 15, 2016 (EP) .................................. 16290242

(51) Int. Cl.
*E21B 49/00* (2006.01)
*G01N 33/28* (2006.01)
(Continued)

(52) U.S. Cl.
CPC .......... *E21B 49/005* (2013.01); *E21B 21/067* (2013.01); *E21B 49/08* (2013.01);
(Continued)

(58) Field of Classification Search
CPC ........ G01N 33/00; G01N 30/00; G01N 30/02; G01N 7/00; G01N 1/2202; G01N 11/02;
(Continued)

(56) References Cited

U.S. PATENT DOCUMENTS 5,746,973 A 5/1998 Naraghi
2001/0029772 A1 10/2001 Binz et al.
(Continued)

FOREIGN PATENT DOCUMENTS

EP 2444802 A1 4/2012
GB 2536975 A 10/2016

OTHER PUBLICATIONS

Search Report Rule 62 EPC issued in European patent application 16290242.3 dated May 18, 2017. 8 pages.

*Primary Examiner* — Harshad R Patel
*Assistant Examiner* — Nigel H Plumb (57) ABSTRACT

The disclosure relates to a modular device for analyzing gas extracted from a drilling fluid used for drilling a wellbore, comprising a chassis having a power supply system, a fluid distribution and regulation system, and a control module, and a first and second analysis module of different types. The analysis modules comprise a detector for measuring a parameter relative to a content of a gas compound. The chassis comprises a core connector having power, communication and fluid outputs, the analysis modules having a module connector complementary to the core connector. The complementary core and module connectors form a removable connection, easy and quick to connect. The device obtains a measurement from the detector of the first analysis module when connected to the chassis via the core connector and a measurement from the detector of the second analysis module when connected to the chassis via the core connector.

16 Claims, 4 Drawing Sheets

(51) Int. Cl.
  *E21B 49/08*   (2006.01)
  *G01N 33/00*   (2006.01)
  *E21B 21/06*   (2006.01)
  *G01N 1/22*    (2006.01)
  *G01N 11/02*   (2006.01)

(52) U.S. Cl.
  CPC ......... *E21B 49/086* (2013.01); *G01N 1/2202* (2013.01); *G01N 11/02* (2013.01); *G01N 33/0031* (2013.01); *G01N 33/2823* (2013.01)

(58) Field of Classification Search
  CPC ........... G01N 33/0031; G01N 33/2823; G01N 33/0013; B01J 19/00; E21B 49/005; E21B 21/067; E21B 49/08; E21B 49/086
  See application file for complete search history.

(56) References Cited

U.S. PATENT DOCUMENTS

| | | |
|---|---|---|
| 2012/0006095 A1 | 1/2012 | Zilioli et al. |
| 2013/0145824 A1 | 6/2013 | Lee et al. |
| 2013/0233057 A1* | 9/2013 | Karoum ................. B01D 53/22 73/31.07 |

* cited by examiner

DEVICE COMPRISING MULTIPLE DETECTORS FOR DETECTING A FLOW OF GAS EXTRACTED FROM A DRILLING FLUID

CROSS REFERENCE TO RELATED APPLICATIONS

This application claims priority to and the benefit of European Patent Application No. 16290242.3, titled "Device and Method for Analyzing at Least a Flow of Gas Extracted from a Drilling Fluid," filed Dec. 15, 2016, the entire disclosure of which is hereby incorporated herein by reference.

BACKGROUND

The disclosure relates to a device and method for analyzing gas contained in a drilling fluid exiting a wellbore.

During the drilling of a petroleum or gas well, it is known how to perform an analysis of the gas drilling compounds contained in the drilling fluid emerging from the well, this fluid being commonly designated as "drilling mud".

This analysis gives the possibility of reconstructing the geological succession of the crossed layers of the formation during the drilling and is involved in the determination of the opportunities of exploiting fluids contained in the formation.

This analysis performed continuously comprises two main phases. A first phase consists in continuously sampling the drilling mud in circulation, and then in bringing it into an extraction enclosure where a certain number of drilling compounds carried by the mud (for example hydrocarbon compounds, carbon dioxide, hydrogen sulfide, helium and nitrogen) are extracted from the mud as a gas.

A second phase consists in transporting the extracted gases towards an analyzer where the composition of these gases are determined and in certain cases, where each of these gases is quantified.

The gases extracted from the mud, mixed with a carrier gas introduced into the degasser are conveyed by suction through a gas extraction conduit up to an analyzer which allows detection of the extracted gases.

SUMMARY

The disclosure relates to a device for analyzing at least a flow of gas extracted from a drilling fluid used for drilling a wellbore, comprising a chassis having a power supply system, a fluid distribution and regulation system, and a control module, and a first and second analysis module of different types, each comprising a detector for measuring parameters relative to a contents of one or several gas compounds in the flow of gas. The chassis comprises a core connector having power, communication and fluid outputs, each of the analysis modules having a module connector complementary to the core connector. The complementary core and module connectors form a removable connection. The device is configured to obtain a measurement from the detector of the first analysis module when the first analysis module is connected to the chassis via the core connector and to obtain a measurement from the detector of the second analysis module when the second analysis module is connected to the chassis via the core connector.

The disclosure also relates to an installation for analyzing drilling fluid in communication with a wellbore comprising a pipe in fluid communication with the wellbore, a sampler for recovering a sample of the fluid in the pipe, an extractor for extracting gas contained in the sample of the drilling fluid, and a device for analyzing the flow of extracted gas as mentioned above, in fluid communication with the or at least one of the extractors.

The disclosure relates to a method of analyzing a flow of gas with a device as mentioned above, comprising measuring a parameter relative to a first gas content of the flow of gas with the device having the first analysis module connected to the core connector, changing the configuration of the analysis device, including disconnecting the first analysis module and connecting the second analysis module to the core connector, and then measuring a parameter relative to a second gas content of the flow of gas with the device having the second analysis module connected to the core connector.

The device, installation and method according to the disclosure enable to perform an analysis of the extracted gas in a flexible manner corresponding to the needs of every rig at every moment, with low on-site installation and maintenance time.

BRIEF DESCRIPTION OF THE DRAWINGS

Various aspects of this disclosure may be better understood upon reading the following detailed description and upon reference to the drawings in which.

DETAILED DESCRIPTION

One or more specific embodiments of the present disclosure will be described below. These described embodiments are examples of the presently disclosed techniques. Additionally, in an effort to provide a concise description of these embodiments, some features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.' In all the following, the terms "upstream" and "downstream" are to be understood relatively to the normal direction of circulation of a fluid in a conduit.

Figure 1:
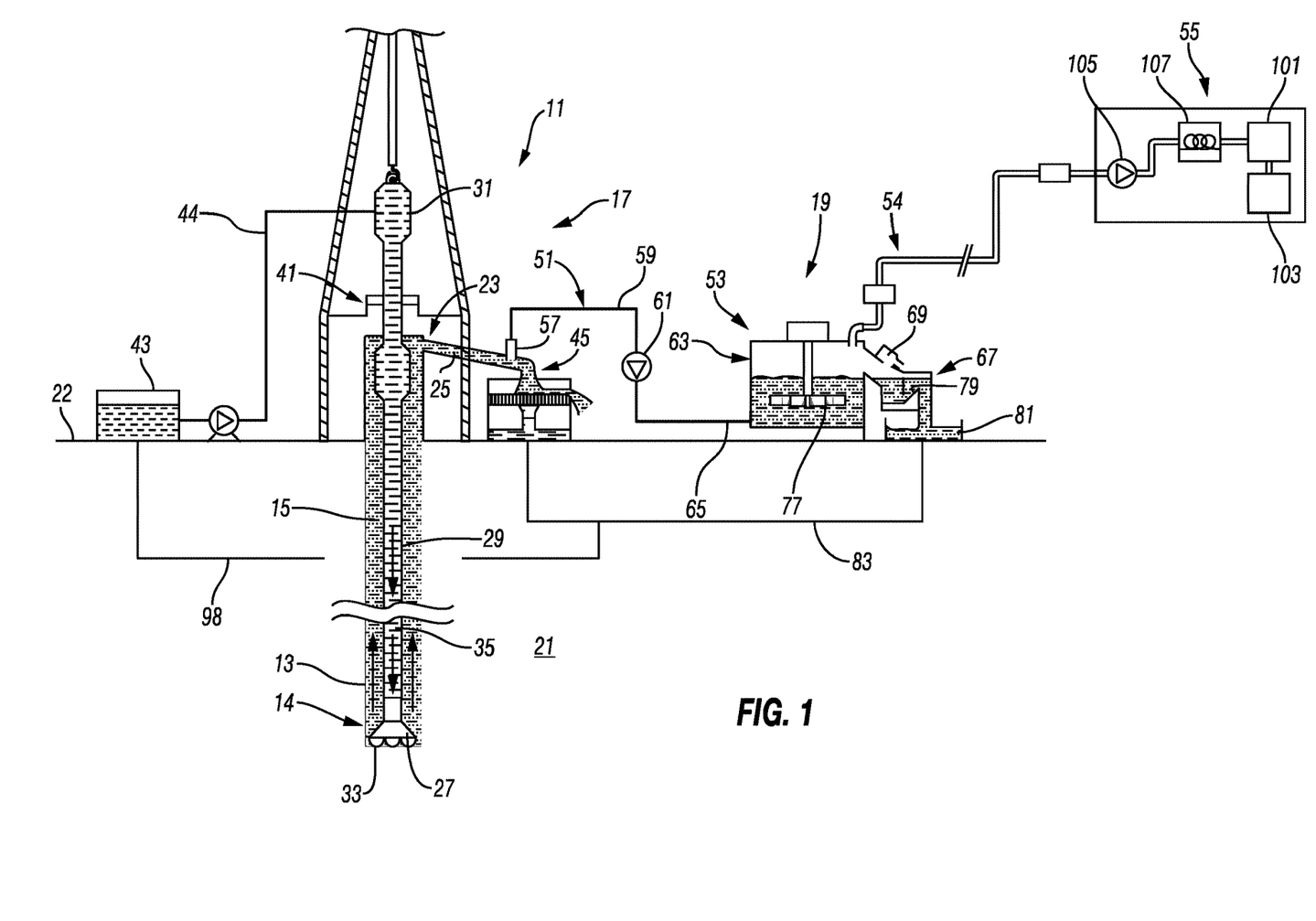
FIG. 1 is a schematic view of an installation for analyzing gas according to an embodiment of the disclosure.

An installation 11 according to an embodiment of the disclosure is illustrated on FIG. 1. The installation 11 comprises a rotary drilling tool 15 drilling a cavity 14; where drilling pipes are placed in the cavity 14, a surface installation 17, and a system 19 for analyzing a drilling fluid.

A borehole 13, delimiting the cavity 14, is formed in a geological formation 21 by the rotary drilling tool 15. At the surface 22, a well head 23 having a discharge pipe 25 closes the borehole 13.

The drilling tool 15 comprises a drilling head 27, a drill string 29 and a liquid injection head 31.

The drilling head 27 comprises a drill bit 33 for drilling through the rocks of the geological formation 21. It is mounted on the lower portion of the drill string 29 and is positioned in the bottom of the drilling pipe 13.

The drill string 29 comprises a set of hollow drilling pipes. These pipes delimit an internal space 35 which makes it possible to bring a drilling fluid from the surface 22 to the drilling head 27. To this end, the liquid injection head 31 is screwed onto the upper portion of the drill string 29. The drilling fluid is a drilling mud, in particular a water-based or oil-based drilling mud. After having flown downwards to the drill bit 33, the drilling fluid flows upwards in the space created between the drill string 35 and the borehole wall 13 and is discharged in a discharge pipe 25 of the surface installation.

The surface installation 17 comprises a support 41 for supporting the drilling tool 15 and driving it in rotation, an injector 43 for injecting the drilling liquid connected to an injection line 44 for transporting drilling fluid and a shale shaker 45.

The injector 43 is hydraulically connected to the injection head 31 via an injection pipe 44 in order to introduce and circulate the drilling fluid in the inner space 35 of the drill string 29.

The shale shaker 45 collects the drilling fluid charged with drilling residues, known as cuttings, said drilling fluid flowing out from the discharge pipe 25. The shale shaker equipped with sieves allows the separation of the solid drilling residues from the drilling mud.

The analysis system 19 comprises a sampler 51 for sampling the mud from the discharge pipe 25, and a gas extractor 53 connected to said sampler 51. The analysis device 19 further comprises an analyzer or analysis device 55 and a line 54, the line 54 allowing the transport of extracted gases from the extractor 53 to said analyzer 55.

The sampler 51 comprise a liquid sampling device 57, connected to the discharge pipe 25, a duct 59 and a peristaltic pump 61 with an adjustable flow rate. The duct 59 connects the liquid sampling device 57 to the gas extractor 53.

The duct 59 may be provided with a mud heater, in order to bring the temperature of the mud to values between 5° C. and 150° C., in particular between 50° C. and 100° C.

The extraction device 53 comprises an enclosure 63, a pipe 65 for supplying mud to the enclosure 63, a pipe 67 for discharging the mud from the enclosure 63, an inlet 69 for introducing a carrier gas into the enclosure 63, tapped in this embodiment into the discharging pipe.

The enclosure 63 is also provided with an agitator 77 mounted in a projecting manner in the enclosure 63 and rotatably driven by a motor mounted on the enclosure 63. The agitator 77 comprises an agitating moving body immersed in the mud.

The pipe 65 for supplying mud extends between the outlet of the peristaltic pump 61 and an inlet opening provided in the lower portion of the enclosure.

The discharge pipe 67 extends between an overflow passage 79 provided in the enclosure 63, and a retaining pit 81 which is to receive the muds discharged from the extractor 53.

The mud introduced into the enclosure 63 via the supply pipe 65 is discharged by overflowing into the discharge pipe 67 through the overflow passage 79. In addition, some of the mud discharged dwells temporarily in the siphon of the discharge pipe 67, which prevents gas from entering the upper portion 75 of the enclosure 63 by way of the lower end of the discharge pipe 67. The introduction of gas into the enclosure 63 is therefore effected purely by the inlet 69 for introducing carrier gas.

The mud collected in the retaining pit 81 is recycled to the injector 43 by way of a pipe 83 for recirculating mud.

The inlet 69 for introducing a carrier gas into the enclosure comprise an air intake mounted on the upstream portion of the discharge pipe 67. This air intake opens into an injection passage in the discharge pipe.

In the example illustrated, the carrier gas is constituted by the air surrounding the installation, at atmospheric pressure, so that the pressure in the enclosure 63 is kept substantially constant at the atmospheric pressure when the injection passage is open.

The extractor disclosed in the above-mentioned embodiment is exemplary may be replaced by any other type of extractor (or gas trap or degasser) able to extract gas contained in a drilling fluid.

The analyzer 55 comprises at least a detector 101 for measuring a parameter relative to the content of one or more gas compounds in the flow of the extracted gases and at least a calculator 103 for obtaining the gas content in view of the measured parameter. The analyzer also comprises in this embodiment a suction system 105 for sucking in the gas contained in the drilling fluid and extracted in the extractor. The suction system 105 may be situated upstream of the detector 101.

The detector 101 comprises, for example, one of the following: FID (flame ionization detector), TCD (thermal conductivity detector), Fourier Transform InfraRed (FTIR) spectrometer, Laser Photo Acoustic Spectrometer (LPAS), Pulse discharge detector (PDD), Photoionization Detector (PID), Electron Capture Detector (ECD) or mass spectrometer (MS). It may also comprise a gas separation module 107, comprising for instance a chromatographic column, for separating the gas compounds before they reach the detector and situated upstream of the detector 101.

The detector may measure a parameter relative to a content of all of the gas compounds (total gas) extracted or relative to the content of one or more of the gas compounds of the flow of extracted gas, such as alkanes, alkene, hydrogen sulfur, etc.

The calculator 103 comprises at least a storage unit for storing a program to derive from the parameter measured by the detector the gas content and a processor to execute the program. It may be a computer. It may also comprise a communication module for communicating with the detector and/or interface for communicating with the user, such as display, keyboard, etc.

Part or the totality of the analyzer 55 may be situated on the rig site, in the vicinity of the wellbore, for instance ATEX 1 zone. In this case, the transport line 54 may be shorter than 10 m. Part or the totality of the analyzer may also be situated away from the wellbore, for instance in a cabin situated out of the ATEX 1 zone at about a few hectometers from the rig site. In particular, the suction system 105, the gas separation module 107 (if any) and the detector 101 are situated at the rig site. The calculator may be situated at the rig site or remotely from the rig site. It may also comprise a plurality of modules, wherein one of the modules may be situated at the rig site, for instance in the detector and at least another of the modules may be situated remotely from the rig site, for instance in the cabin or at a supervision center for supervising a plurality of rig sites.

Figure 2:
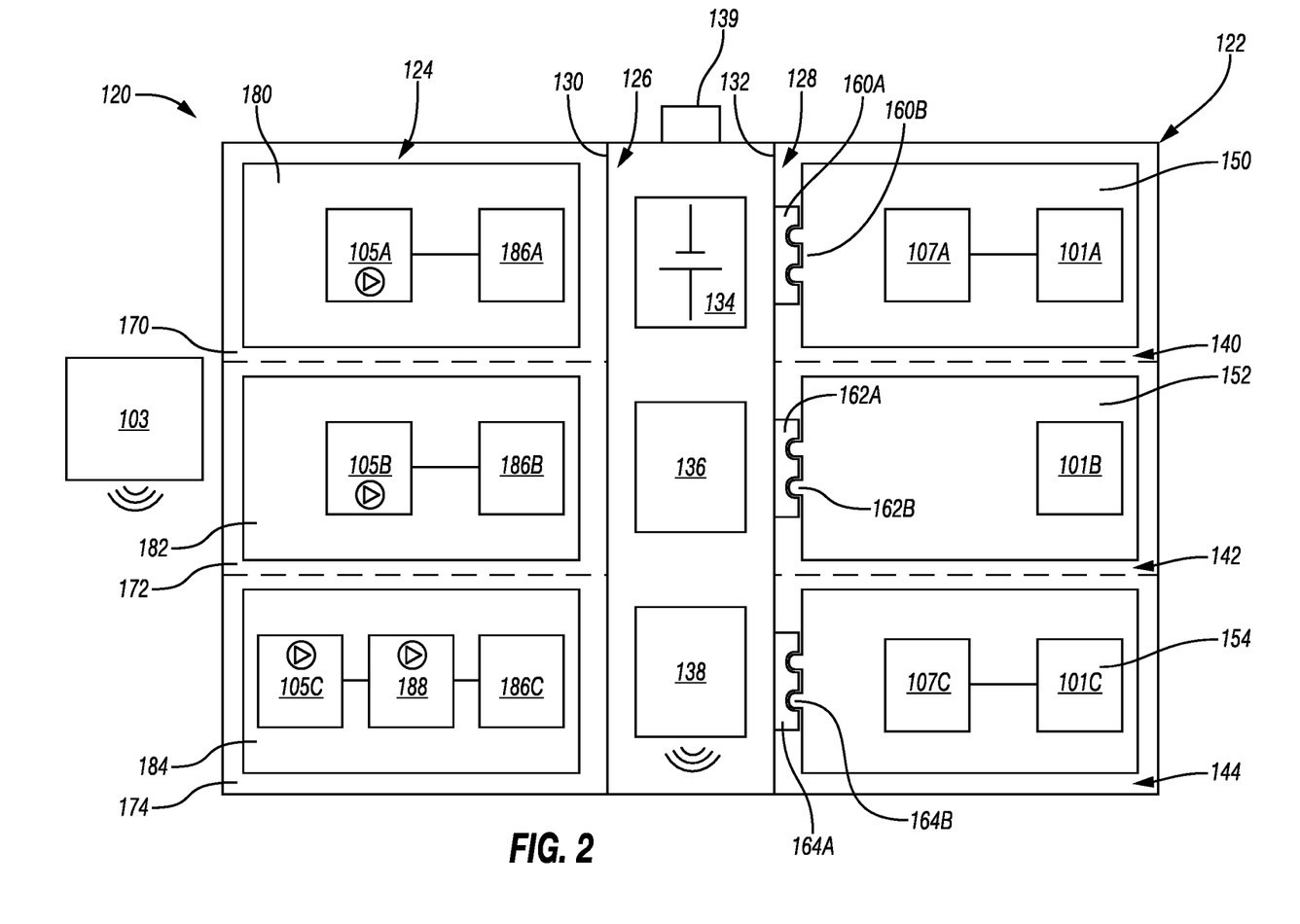
FIG. 2 is a schematic view of an analysis device according to an embodiment of the disclosure.

FIG. 2 shows a representation of at least part of the analysis device 55 of FIG. 1 according to an embodiment of the disclosure.

The analysis device 55 of FIG. 2 comprises a measuring device 120 comprising at least a suction system 105 such as a pump and a detector 101. This analysis device is linked to a remote calculator 103 being for instance a personal computer displaying to an user the results of the measuring device.

The measuring device 120 as shown on FIG. 2 comprises three analytical lines each having at least a suction system 105A, 105B, 105C and a detector 101A, 101B, 101C. The measuring device comprises a chassis 122 forming an enclosure having three compartments 124, 126 and 128 separated by walls 130, 132. In the embodiment of FIG. 2, the compartments are disposed in a row along the longitudinal axis of the measuring device 120. However, one of the compartment for instance 126 may very well be disposed below the two others. Generally, any arrangement of the compartments may be considered.

The first compartment 126 of the chassis or core compartment comprises several functional elements of the measuring device 120, such as a power supply system 134, that may be or may not be connected to an external power source, a gas distribution and regulation system 136 for guiding the gas coming from the extractor, and potentially other sources of gas used for distribution and regulation purposes, in the measuring device. Such system 136 may for instance comprise fluid circuits comprising manifolds, valves, pressure regulators and flow regulators. The core compartment 126 also comprises a control unit 138 for controlling the elements inside of the measuring device and communicating with elements outside of the measuring device such as the calculator 103 for instance via a wireless network. The control unit may comprise a processor, a storage unit that stores programs to be executed by the processor and a communication unit. The chassis also comprises an interface 139 for interfacing with elements outside of the measuring device 120, for instance gas line(s) such as line 54 or line for bringing to the analyzer any other consumable gas needed for the analysis (for instance, carrier gas) and electrical lines. The interface may comprise one or several input ports.

The second compartment 128 of the chassis or analytical compartment comprises three slots 140, 142 and 144 for receiving three analysis modules, respectively a first 150, a second 152, and a third analysis module 154. The slots 140-144 are of predetermined dimensions as well as the analysis modules 150-154, the chassis being configured so that the slots have dimensions complementary to the dimensions of the analytical modules. The slots are exactly identical, which means that a same analysis module that may be inserted in one slot may be inserted in any other of the slots. The second compartment comprises at a first end, situated on the wall 132 separating the second compartment from the core compartment, a core connector, respectively 160A, 162A, 164A, which is an hybrid connector having fluid, power and communication outputs The analysis modules 150-154 have at one of their end a module connector 160B, 162B, 164B, complementary of the core connector. Connectors 160A, 162A and 164A are identical enabling to each of the analysis module to connect to the chassis in any of the slots 140-144. Connectors are configured so that the connection between chassis 122 and each of the analysis module is removable and may be established in only one operation.

Each of the analysis module comprises at least a detector, respectively 101A, 101B and 101C. At least one of the analysis module (here 150 and 154) may also comprises a gas separation module, respectively 107A and 107C. The analysis modules also comprises inside of the modules the electrical and fluidic connections able to power the detector, to direct the gas extracted from the drilling fluid from the connector 160, 162, 164 to the detector 101A, 101B, 101C, optionally via the gas separation module 107A, 107C and to deliver the measured parameters to the control unit 138. Detector 101A-101C and gas separation module 107A-107B may be heated and insulated and include any element, such as a heater, necessary to obtain this result.

Analysis module may be of the same type of or different types. For instance, here, the first analysis module 150 comprises a detector 101A of the first type, for instance a mass spectrometer of a Laser PhotoAcoustic spectrometer and a gas chromatograph upstream from the detector for separating the gas compounds extracted from the drilling fluid. The detector 101A may then measure the content of each of the gas compound separated by the gas chromatograph. The third analysis module 154 may be exactly the same as the first analysis module.

The second analysis module 152 may comprise a detector 101B of the second type, for instance a TCD (Thermal Conductivity Detector) or FID (Flame Ionization Detector). The second analysis module may measure the total content of gas extracted from the drilling fluid.

The analysis compartment comprises an access lid (not shown) for instance in top wall of compartment in order to access from the outside of the enclosure inside of the compartment and to connect and disconnect each of the analysis modules when needed. The lid may be provided with a particular locking element if necessary.

The third compartment or pumping compartment 124 comprises as well three slots 170, 172, 174 for receiving three pump modules, respectively 180, 182, 184. Each pump module comprises a pump 105A, 105B, 105C and is connected to the core compartment via power, command and fluid connections. In particular, each of the pump modules is electrically connected to the power supply system 134 and to the control module 138 and is in fluid communication with the gas distribution system 136. The pump modules 184 may comprise a drier 186A-186C for instance situated downstream of the pump 105B and one of the pump module 184 may comprise two pumps in series or in parallel, the second pump being here designated by 188.

The connection between the pump module and the core compartment may also be set with an hybrid connector having power, communications and fluidic outputs as core connectors 160-164 or with several independent connectors, such as pipes, cables, etc.

The pump compartment may also comprise an access lid (not shown) for instance in top wall of compartment in order to access from the outside of the enclosure inside of the compartment and to connect and disconnect each of the pump modules when needed. The lid may be provided with a particular locking element if necessary. It may not be the same locking element as for the analysis compartment as the right to access this compartment may not be the same.

A first analytical line of the measuring device 120 comprises the first analysis module 150 and the pump module 180. Both are in fluid communication via the gas distribution and regulation system configured via the control module so that the detector is able to deliver a measurement. The control module is also able to configure the pump, for instance the flow of the pump 105A of pump module 180 so that the measurement of the detector is optimized.

Similarly, a second analytical line comprises the second pump module 182 and second analysis module 142 and a third analytical line comprises the third pump module 184 and third analysis module 144.

If the three lines are meant to analyze the gas exiting the wellbore from line 54, the control unit 138 may for instance configure the gas distribution unit so that it separates the flow in three subflows, each directed to a pump module and the pump settings so that the pumps generate a flow of gas appropriate for the detector of the same analytical line connected to the pump via the gas distribution system 136.

Of course, the arrangement of the pump modules may be different from the disclosed arrangement. Depending on the connections set with the gas distribution system 136, pump module 182 could be in fluid communication with first analysis device 140 for instance. The gas distribution system may also be configured so that it is able to take several configuration in order to connect any pump module with any analysis module depending on the commands of the control unit.

A slot of the measuring device may also be empty, in which case the control module controls the systems 134, 136 and if needed the pump module associated to the connector provided in said slot so that no power and no fluid is delivered at the connector.

An analyzer may also comprises any number of analytical lines and of analysis modules. Depending on the architecture of the analyzer, a same pump may also be associated to two analysis modules.

An analyzer according to the embodiment of FIG. 2 may be used for several measurements. For instance, the analysis modules may be all used to analyze gas from the drilling fluid exiting the wellbore. The second analysis module 152 analyzes the total gas coming from a sample of the drilling fluid while the first analysis module measures a parameter relative to specific gas compounds separated by the gas chromatograph such as alkanes having less than 5 atoms of carbon, and the third analysis module 154 is used to measures a parameter relative to other specific gas compounds such as alkanes having from 6 to 9 or 6 to 12 atom carbons from the same drilling fluid. In another embodiment, the first analysis module measures a parameter relative to alkanes having from 2 to 5 atoms and the third analysis module measures a parameter relative to methane having $^{12}$C and $^{13}$C carbon atoms (isotopic measurements). Any other combination is possible.

When the analyzer is set up to analyze gas coming from drilling fluid exiting the wellbore on all of the analytical lines, the interface 139 may comprise several entries (for instance, one entry per analytical lines), wherein the flow is divided in three or directed in turn to the first, the second and the third analytical line via a distribution system upstream of the interface 139. Alternatively, the interface 139 may comprise only one entry and the separation between the three flows is performed in the gas distribution system.

The analyzer 55 may also be used to measure parameters from drilling fluid coming from several locations in the drilling fluid circulation system. For instance, two analytical lines may be used to analyze gas coming from the transport line 54 while one line may be used to measure a parameter from a gas coming from another drilling fluid line, such as the injection line 44 for injecting mud into the wellbore.

Such analyzer is particularly convenient for comparing two flows of drilling fluid, such as isotopic content or content of alkanes and for instance determining to which extent the gas is reinjected in the wellbore when drilling fluid is recirculated. Analysis may be performed in real-time.

Therefore, the analyzer according to the disclosure is flexible and is able to analyze any gas coming from any location of the rig. It is possible in a first configuration to connect all three analytical lines to transport line 54 and in a second configuration to connect one or two input ports of the interface 139 only to the transport line 54 and connect the other to other gas transport lines coming from any location of the rig. The analysis modules may also be changed very easily depending on the configuration of the analyzer and the parameters that are seeked to be measured.

Figure 3:
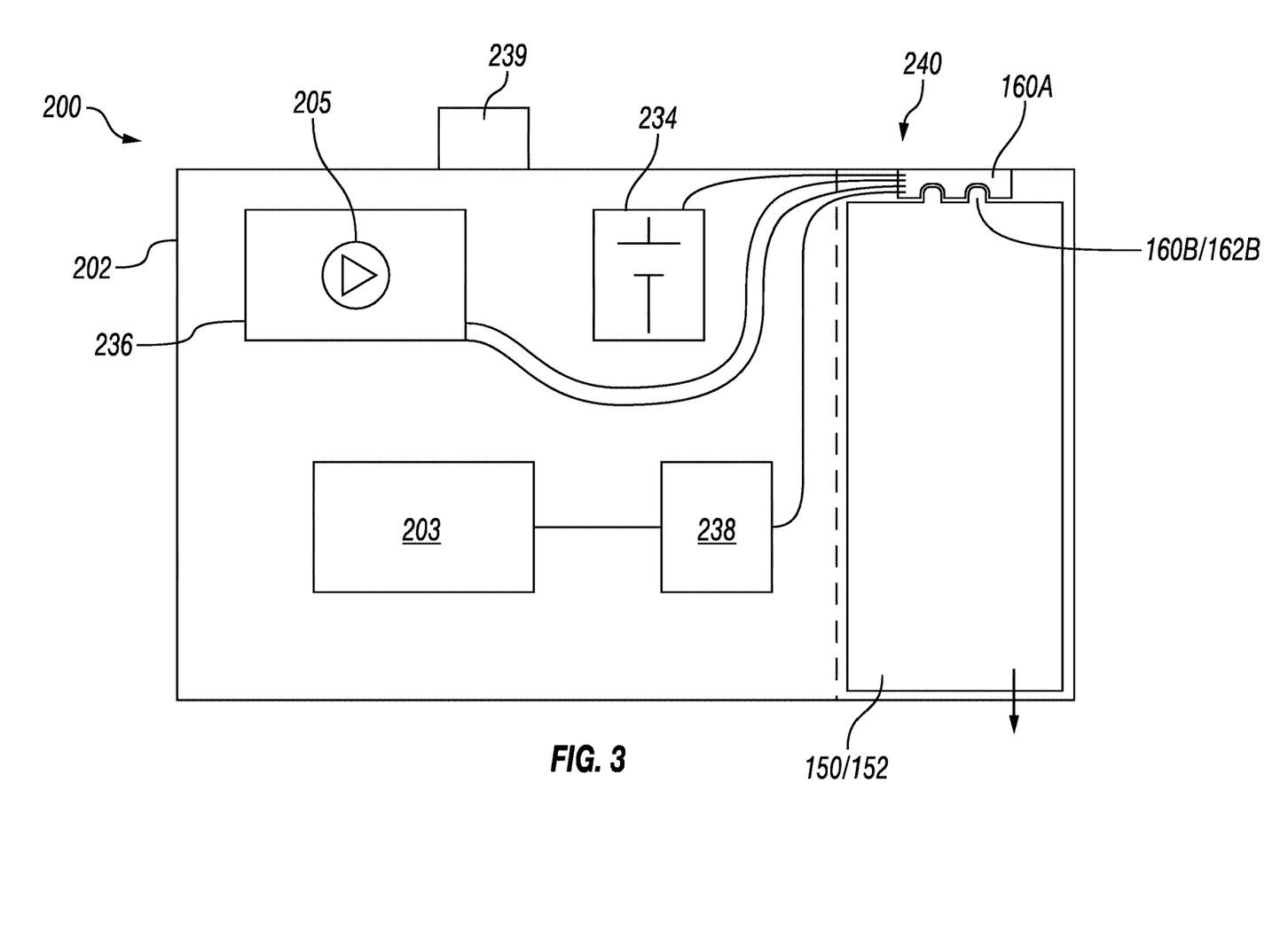
FIG. 3 is a schematic view of an analysis device according to another embodiment of the disclosure.

In another more simple embodiment shown on FIG. 3, the analyzing device 200 comprises a chassis having an enclosure 202 and comprising only a slot such as 240 having a core connector 160A for receiving an analysis module 150 or 152 for instance, each having a complementary module connector, respectively 160B or 162B.

The enclosure also comprises as previously disclosed a power supply system 234, a gas distribution system 236 comprising a pump 205 and a control unit 238. It also comprises an interface 239 with the outside of the enclosure. The interface 239 enables to connect for instance with a gas line 54. In this embodiment the pump is included in the gas distribution system and not situated in a separate module. All the systems 234-238 are connected to the connector 160A on one side. They may be also connected to the interface 239 on the other side, which is the case concerning at least the gas distribution system 236.

In this embodiment, the enclosure 202 also comprises a calculator 203 and the content determination of the gas extracted is performed directly in the enclosure 202.

This enclosure also comprises a lid enabling to open the enclosure and to access to the analysis module. The analysis module may then be changed from a first to a second analysis module easily via core connector 160A and complementary module connectors 160B, 162B. When the analysis module changes, the control module may also communicate with the gas distribution system and power supply system in order to change their configuration (if necessary) to adapt to the analysis module connected in the enclosure.

Devices shown on FIG. 2-3 are only exemplary devices according to particular embodiments of the disclosure. A device having any number of analysis and pump modules may be manufactured according to the disclosure. Further, the device may comprise embodiments in which the gas and regulation system is configured so that two pumps are in fluid communication with a same analysis module in order to generate for instance alternative cycles. At least a detector may also be included inside the chassis and not inside an analysis module.

Figure 4:
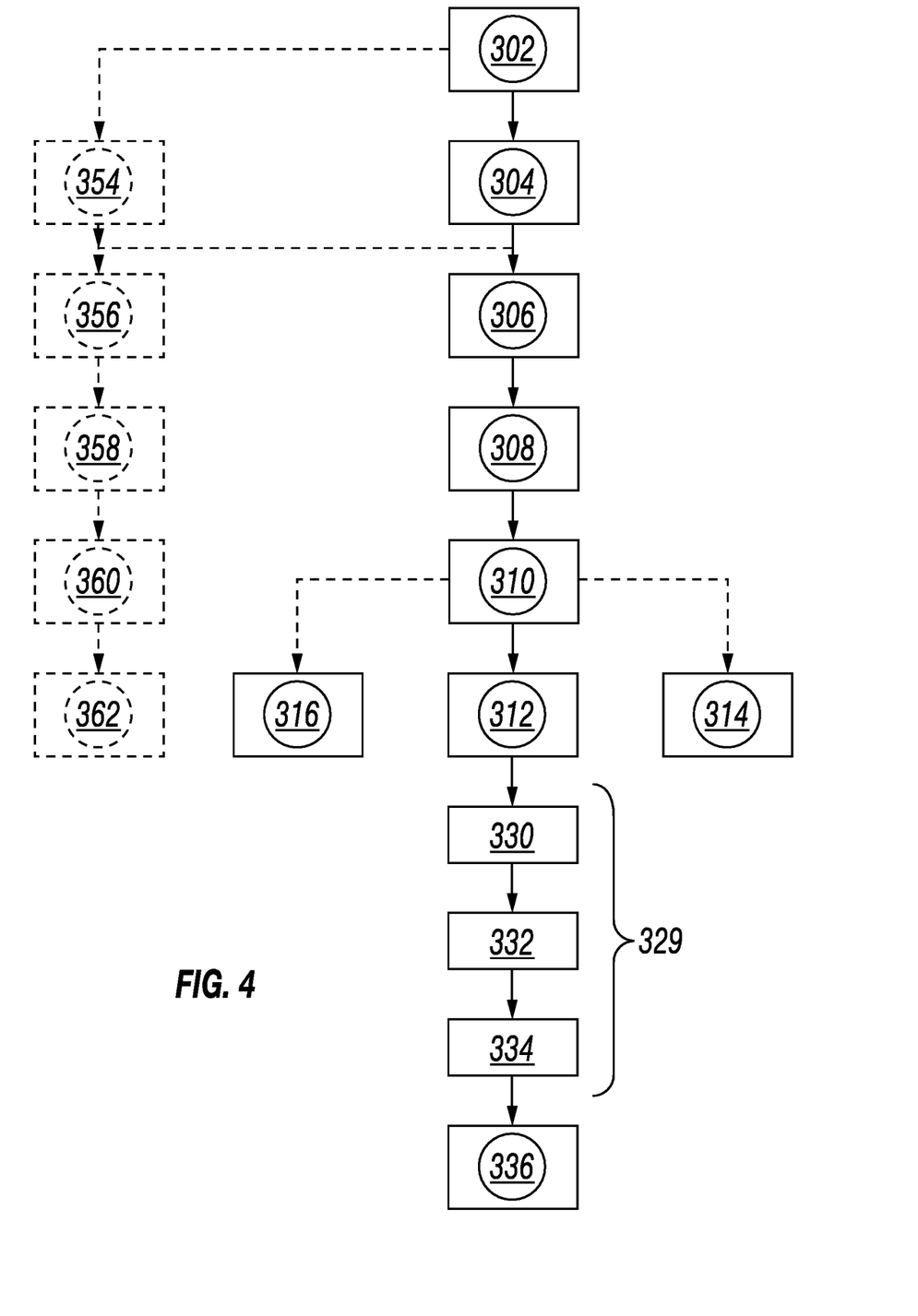
FIG. 4 is a flowchart of a method for analyzing gas according to an embodiment of the disclosure.

Referring to FIG. 4 a method 300 for analyzing a gas coming from a drilling fluid will be described.

The method 300 first comprises circulating a drilling fluid in a wellbore (block 302). It also comprises recovering a sample of the drilling fluid at the exit of the wellbore, in particular in the discharge pipe 25, with a sampler such as sampler 51 (at block 304).

It also comprises transporting a drilling fluid to an extractor 53. In the installation of FIG. 1, this flow is transported to extractor 53 in line 51 via pump 61 (block 306) and extracting gas contained in the drilling fluid and in particular at least a gas compound contained in the drilling fluid such as an hydrocarbon including an alkane, hydrogen sulfide (H2S) or Helium (block 308).

When extraction has been performed, extracted gas is recovered and transported to the analyzer with the carrier gas (block 310) via gas outlet of the extraction cell and transport line 54. It is then analyzed (block 312) in order to quantify the contents of one or several gas compounds as the ones disclosed above in the drilling fluid. Depending on the analysis, gas compounds are separated via gas chromatography or not.

The analysis is performed by the analysis device such as the one shown on FIG. 2-3 comprising interchangeable analysis modules. For instance, analysis at block 312 is performed with the help of the analysis module 150 of the analyzer of FIG. 2. Analysis comprises measuring a parameter relative to the extracted gas and deriving from the parameter a gas content and optionally displaying the gas content to an user.

As explained previously, simultaneous optional analysis (blocks 314, 316) may be performed when the analysis device comprises several analytical lines. For instance, when using the analyzer of FIG. 2, the analysis at blocks 314, 316 may be carried out by second and third analysis modules 152, 154.

All of these operations are operations that are performed continuously which is shown on the flow diagram by representing them with a circle in the square box.

Further operations 306-312 may be performed simultaneously in another locations of the rig (blocks 354-362) for analyzing gas contained in drilling fluid sampled at another location of the wellbore (as shown by arrow 320) or at the same location but extracted with another extractor (as shown by arrow 322). Of course the analysis operations (blocks 312-316 and 362) may be performed in the same measuring devices 120, 202 or in different ones.

When the analysis operation has been performed and it is decided to change the measured parameter of the extracted gas flow, the method comprises changing the configuration of the analyzer (block 329). This is performed by removing the analysis module 150 from the chassis (block 330) and connecting the chassis to another analysis module such as 152 or 154 (block 332). Changing the configuration may consist only in unplugging analysis module's 150 module connector 160B from core connector 160A and introducing the standard module connector of another module 152 into the connector 160A of the chassis. Changing the configuration may also comprise changing the lines connected to the input port(s) 139 but this operation is optional and not shown on FIG. 4. While the analysis module is changed, the sampling and extraction may be stopped or the extracted gas may be directed to an exhaust port which may be gas port of connector 160A.

Then, changing the configuration of the analysis device comprises determining and changing the settings of the different systems 134, 136, 138/234-238 of the chassis so as to operate correctly the new analysis module (block 334). For instance, block 334 comprises sending a message to the analysis module via the control module to detect the type of analysis module and determine associated settings of the analysis module and then sending commands to the gas distribution system, the power supply system and the pump so as to change their configuration if needed, in order to adapt their settings to the ones of the new analysis module. The control module may also communicate with the calculator in order to modify the settings of the calculator (calibration to use in function of measurement received, interface to display to the user, etc.) in view of the type of the analysis module that is used. At block 336, analysis with the new module may be carried out.

The analysis device according to the disclosure is therefore flexible as it enables to change quickly and easily the type of analysis performed on the rig in function of the particular rig or of a particular job. Further, when setting up the analysis module, or changing the configuration of the analysis device, the analysis device does not necessitate a long installation time, being in a plug n' play mode. Such analysis device may be compact and may be installed on a rig, directly next to the extractor, in ATEX zone 1 or in a cabin out of the ATEX 1 zone. Such analysis device also enables an easy maintenance in view of its modular architecture and may enable to save substantial costs as the same analysis device may be installed to several rigs even though the analysis performed are not the same.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

The disclosure generally relates to a device for analyzing at least a flow of gas extracted from a drilling fluid used for drilling a wellbore, comprising:
    a chassis having at least:
        a power supply system
        a fluid distribution and regulation system,
        a control module,
    at least a first and second analysis module of different types, each comprising at least a detector for measuring at least a parameter relative to a content of at least a gas compound in the flow of gas,
wherein the chassis comprises a core connector having power, communication and fluid outputs, each of the analysis modules having a module connector complementary to the core connector, wherein the complementary core and module connectors are configured to form a removable connection, and wherein the device is configured to obtain a measurement from the detector of the first analysis module when the first analysis module is connected to the chassis via the core connector and to obtain a measurement from the detector of the second analysis module when the second analysis module is connected to the chassis via the core connector.

The first analysis module may be configured to measure a parameter relative to at least a first content of gas, while the second analysis module may be configured to measure a parameter relative to at least a second content of gas, wherein the first and second gas content are distinct.

The first and second content of gas may comprise at least one of the following:
    total content of gas contained in the drilling fluid
    content of a gas compound contained in the drilling fluid, wherein the gas compound is preferably one of an alkane having less than 12 carbon atoms, an alkene, an hydrogen sulfur or helium.

In particular, each of the first and second analysis module may be configured to detect one of the following: a total content of gas contained in the drilling fluid, a content of each alkane having between P and Q carbon atoms contained in the drilling fluid, wherein P and Q are between 1 and 12; a content of an isotopic alkane having between P and Q carbon atoms contained in the drilling fluid, wherein P and Q are between 1 and 12; a content of ethene contained in the drilling fluid, or a content of hydrogen sulfur or helium.

Alternatively, or additionally, the first analysis module may comprise a first type of detector, while the second analysis module may comprise a second type of detector.

The detector of the first analysis module and/or second analysis module is one of the following:
Flame Ionization Detector,
Thermal Conductivity Detector,
Mass Spectrometer,
Laser Photoacoustic Spectrometer.
Fourier Transform Infrared Spectrometer
PhotoIonization Detector (PID),
Electron Capture Detector (ECD),
Pulse discharge detector (PDD).

At least one of the first or second analysis module may comprises a gas separation module upstream from the detector for separating the gas compounds contained in the flow of gas.

The control module of the chassis may be configured to control the power supply (delivered by the power supply system) to the core connector and/or the flow of gas delivered to the core connector (delivered by or via the gas distribution and regulation system) in function of the type of the analysis module connected to the core connector.

The device may comprise at least a pump for delivering the flow of gas to the detector, in fluid communication with the core connector, for instance via the fluid distribution and regulation system. The control module of the chassis may be configured to control the flow delivered by the pump in function of the type of the analysis module connected to the core connector.

The pump may be included in the fluid distribution and regulation system or a separate module. In a particular embodiment, the device may have at least a pump module comprising the pump, connected to the chassis via at least one removable power, communication and fluid connection.

The chassis may comprise at least two core connectors configured so that one analysis module is connected to the first core connector while another analysis module is connected to the second core connector.

The device may also comprise at least two pump modules, wherein the fluid distribution and regulation system of the chassis is configured so that:
a first pump module is in fluid communication the first core connector and the corresponding analysis module,
a second pump module is in fluid communication with the second core connector and the corresponding analysis module.

The fluid distribution and regulation system may take several configurations so that each of the first and second pump modules are in fluid communication with any of the first and second analysis modules.

The chassis may comprise an enclosure for enclosing the power supply system, the fluid distribution and regulation system, the control module, at least one core connector, an analysis module connected to each of the connector, and optionally at least a pump module.

The enclosure comprises a core compartment containing the power supply system, the fluid distribution and regulation system, the control module and an analysis compartment in which are disposed the at least one core connector, the at least one analysis compartment comprising and opening for introducing the analysis modules and connecting each of them to a core connector, and a lid for closing the opening.

The device may also comprise at least a pumping compartment comprising the at least one pump module.

The disclosure also relates to an installation for analyzing drilling fluid in communication with a wellbore comprising:
at least a pipe in fluid communication with the wellbore,
at least a sampler for recovering a sample of the fluid in the pipe,
at least an extractor for extracting gas contained in the sample of the drilling fluid,
a device according to any embodiment disclosed hereinabove, in fluid communication with the or at least one of the extractors for analyzing the corresponding flow of extracted gas.

The installation according may also comprise a transport line between the extractor and the device, wherein the transport line is not longer than 10 meters.

The installation may also comprise:
a first pipe, a first sampler for recovering a first sample of the fluid in the first pipe and a first extractor for extracting gas contained in the first sample,
a second pipe, a second sampler for recovering a second sample of the fluid in the second pipe and a second extractor for extracting gas contained in the first sample,
wherein the device has at least two core connectors and comprises a third analysis module, of the same type as the first analysis module, wherein the first analysis module is connected to the first core connector and is in fluid communication with the first extractor while the third analysis module is connected to the second core connector and is in fluid communication with the second extractor. The disclosure also related to a method of analyzing a flow of gas with a device according to any of the embodiments disclose above, comprising:
measuring at least a parameter relative to at least a first gas content of the flow of gas with the device having the first analysis module connected to the core connector,
changing the configuration of the analysis device, comprising
disconnecting the first analysis module and
connecting the second analysis module to the core connector,
measuring at least a parameter relative to at least a second gas content of the flow of gas with the device having the second analysis module connected to the core connector,
Changing the configuration of the analysis device may comprise:
Verifying the type of the second analysis module,
Determining settings of the second analysis module,
Commanding at least one of the gas distribution and regulation system, the power supply system, the calculator or the pump in function of the settings of the second analysis module.

The invention claimed is:
1. A device for analyzing at least a flow of gas extracted from a drilling fluid used for drilling a wellbore, comprising:
a chassis having at least:
a power supply system
a fluid distribution and regulation system,
a control module,
at least a first and second analysis module of different types, each comprising at least a detector for measuring at least a parameter representative of a content of at least a gas compound in the flow of gas, wherein the chassis comprises a core connector having power, communication and fluid outputs, each of the analysis modules having a module connector complementary to the core connector, wherein the complementary core and module connectors are configured to form a removable connection, and wherein the device is configured to obtain a measurement from the detector of the first analysis module when the first analysis module is connected to the chassis via the core connector and to obtain a measurement from the detector of the second analysis module when the second analysis module is connected to the chassis via the core connector, wherein the control module of the chassis is configured to control the power delivered to the core connector and/or the flow of gas delivered to the core connector in function of the type of the analysis module connected to the core connector.

2. The device according to claim 1, wherein the first analysis module is configured to measure a parameter representative of content of at least a first gas, while the second analysis module is configured to measure a parameter representative of content of at least a second gas, wherein the first and second gas are distinct.

3. The device according to claim 2, wherein the content of at least a first or second gas comprise at least one of the following:
   total content of gas contained in the drilling fluid
   content of a gas compound contained in the drilling fluid.

4. The device of claim 3, wherein the gas compound is one of an alkane having less than 12 carbon atoms, an alkene, an hydrogen sulfur or helium.

5. The device according to claim 1, wherein the detector of the first analysis module and/or second analysis module is one of the following:
   Flame Ionization Detector,
   Thermal Conductivity Detector,
   Mass Spectrometer,
   Laser Photoacoustic Spectrometer,
   Fourier Transform Infrared Spectrometer
   PhotoIonization Detector (PID),
   Electron Capture Detector (ECD),
   Pulse discharge detector (PDD).

6. The device according to claim 1, wherein at least one of the first or second analysis module comprises a gas separation module upstream from the detector for separating the gas compounds contained in the flow of gas.

7. The device according to claim 1, comprising at least a pump for delivering the flow of gas to the detector, in fluid communication with the core connector, wherein the control module of the chassis is configured to control the flow delivered by the pump in function of the type of the analysis module connected to the core connector.

8. The device according to claim 1, having at least a pump module comprising the pump, wherein the pump module is connected to the chassis via at least one removable power, communication and fluid connection.

9. The device according to claim 8, wherein the chassis comprises at least two core connectors configured so that one analysis module is connected to the first core connector while another analysis module is connected to the second core connector, wherein the device comprises at least two pump modules, wherein the fluid distribution and regulation system of the chassis is configured so that:
   a first pump module is in fluid communication the first core connector and the corresponding analysis module,
   a second pump module is in fluid communication with the second core connector and the corresponding analysis module.

10. The device according to claim 1, wherein the chassis comprises at least two core connectors configured so that one analysis module is connected to the first core connector while another analysis module is connected to the second core connector.

11. The device according to claim 1, wherein the chassis comprises an enclosure for enclosing the power supply system, the fluid distribution and regulation system, the control module, the core connector, an analysis module connected to each of the connector.

12. The device according to claim 11, wherein the enclosure comprises a core compartment containing the power supply system, the fluid distribution and regulation system, the control module and an analysis compartment in which are disposed the at least one core connector, the at least one analysis compartment comprising and opening for introducing at least one of the first and second analysis module and connecting said module to the core connector, and a lid for closing the opening.

13. An installation for analyzing drilling fluid in communication with a wellbore comprising:
   at least a pipe in fluid communication with the wellbore,
   at least a sampler for recovering a sample of the fluid in the pipe,
   at least an extractor for extracting gas contained in the sample of the drilling fluid,
   a device according to claim 1, in fluid communication with the or at least one of the extractors for analyzing the flow of extracted gas.

14. The installation according to claim 13, comprising a transport line between the extractor and the device, wherein the transport line is no longer than 10 meters.

15. A method of analyzing a flow of gas with a device according to claim 1, comprising:
   measuring at least a parameter representative of a content of at least a first gas in the flow of gas with the device having the first analysis module connected to the core connector,
   changing the configuration of the analysis device, comprising
      disconnecting the first analysis module and
      connecting the second analysis module to the core connector,
   measuring at least a parameter representative of a content of at least a second gas in the flow of gas with the device having the second analysis module connected to the core connector.

16. The device according to claim 1, wherein the chassis comprises an enclosure for enclosing at least a pump module.

* * * * *